United States Patent
Winslow et al.

(10) Patent No.: US 8,425,614 B2
(45) Date of Patent: *Apr. 23, 2013

(54) MODULAR CENTER PEGGED GLENOID

(75) Inventors: Nathan A. Winslow, Warsaw, IN (US);
Brian K. Berelsman, Warsaw, IN (US);
Russell M. Parrott, Winona Lake, IN (US); Bryce A. Isch, Bluffton, IN (US);
Thomas M. Vanasse, Warsaw, IN (US);
Kane Wu, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 211 days.

This patent is subject to a terminal disclaimer.

(21) Appl. No.: 12/835,223

(22) Filed: Jul. 13, 2010

(65) Prior Publication Data

US 2011/0035013 A1 Feb. 10, 2011

Related U.S. Application Data

(63) Continuation-in-part of application No. 11/385,035, filed on Mar. 20, 2006, now Pat. No. 7,753,959.

(51) Int. Cl.
*A61F 2/40* (2006.01)
(52) U.S. Cl.
USPC .................................. 623/19.11; 623/19.13
(58) Field of Classification Search .... 623/19.11–19.14, 623/22.33–22.38
See application file for complete search history.

(56) References Cited

U.S. PATENT DOCUMENTS

| | | | |
|---|---|---|---|
| 3,803,641 A | 4/1974 | Golyakhovsky | |
| 3,916,451 A | 11/1975 | Buechel et al. | |
| 3,979,778 A | 9/1976 | Stroot | |
| 4,042,980 A | 8/1977 | Swanson et al. | |
| 4,045,825 A | 9/1977 | Stroot | |
| 4,045,826 A | 9/1977 | Stroot | |
| 4,206,517 A | 6/1980 | Pappas et al. | |
| 4,355,429 A | 10/1982 | Mittelmeier et al. | |
| 4,550,450 A | 11/1985 | Kinnett | |
| 4,725,280 A | 2/1988 | Laure | |
| 4,865,605 A | 9/1989 | Dines et al. | |
| 4,919,669 A | 4/1990 | Lannelongue et al. | |
| 4,964,865 A | 10/1990 | Burkhead et al. | |
| 4,964,867 A | 10/1990 | Boger | |
| 4,986,833 A | 1/1991 | Worland | |
| 5,030,219 A | 7/1991 | Matsen, III et al. | |
| 5,032,132 A | 7/1991 | Matsen, III et al. | |
| 5,080,673 A | 1/1992 | Burkhead et al. | |
| 5,108,446 A | 4/1992 | Wagner et al. | |
| 5,360,452 A | 11/1994 | Engelhardt et al. | |
| 5,437,677 A | 8/1995 | Shearer et al. | |
| 5,489,309 A | 2/1996 | Lackey et al. | |
| 5,489,310 A | 2/1996 | Mikhail | |
| 5,512,145 A | 4/1996 | Hollenberg | |
| 5,549,691 A | 8/1996 | Harwin | |
| 5,593,448 A | 1/1997 | Dong | |

(Continued)

*Primary Examiner* — Thomas J Sweet
*Assistant Examiner* — Megan Wolf
(74) *Attorney, Agent, or Firm* — Harness, Dickey (57) ABSTRACT

A glenoid component used for shoulder arthroplasty is adapted to be implanted into a scapula and engaged by a head of a humeral component. The glenoid component includes a body having a first articulating surface and a second medial surface opposite to the first articulating surface. The first articulating surface is adapted to engage with a humeral head. A plurality of removable fixed pegs each have a first end adapted to engage a cavity formed in the scapula and a second end extending from the medial surface. A central peg fixation mechanism is provided that is configured to couple an optional central fixation peg to the medial surface.

10 Claims, 12 Drawing Sheets

U.S. PATENT DOCUMENTS

| | | |
|---|---|---|
| 5,702,447 A | 12/1997 | Walch et al. |
| 6,102,951 A | 8/2000 | Sutter et al. |
| 6,228,119 B1 | 5/2001 | Ondrla et al. |
| 6,245,074 B1 | 6/2001 | Allard et al. |
| 6,277,390 B1 | 8/2001 | Schaffner |
| 6,364,910 B1 | 4/2002 | Shultz et al. |
| 6,379,386 B1 | 4/2002 | Resch et al. |
| 6,406,495 B1 | 6/2002 | Schoch |
| 6,448,315 B1 | 9/2002 | Lidgren et al. |
| 6,506,214 B1 | 1/2003 | Gross |
| 6,506,216 B1 | 1/2003 | McCue et al. |
| 6,514,287 B2 | 2/2003 | Ondrla et al. |
| 6,673,115 B2 | 1/2004 | Resch et al. |
| 6,699,289 B2 | 3/2004 | Iannotti et al. |
| 6,761,740 B2 | 7/2004 | Tornier et al. |

MODULAR CENTER PEGGED GLENOID

CROSS-REFERENCE TO RELATED APPLICATIONS

This application is a continuation-in-part application of U.S. patent application Ser. No. 11/385,035, filed on Mar. 20, 2006, now U.S. Pat. No. 7,753,959, issued on Jul. 13, 2010. The entire disclosure of the above application is incorporated herein by reference.

FIELD

The present disclosure relates to a prosthetic device and, more particularly, to a modular glenoid prosthetic.

BACKGROUND

The statements in this section merely provide background information related to the present disclosure and may not constitute prior art. A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus can be resected and a cavity is created in the intramedullary canal of the host humerus for accepting a humeral component. The humeral component includes a head portion used to replace the natural head of the humerus. Once the humeral component has been implanted, the glenoid cavity positioned at the lateral edge of the scapula may also be resurfaced and shaped to accept a glenoid component. The glenoid component generally includes an articulating surface which is engaged by the head portion of the humeral component.

It is generally known in the art to provide a shoulder joint prosthesis having a glenoid component, as discussed above. However, the current prior art glenoid components along with the associated surgical components and instruments utilized during shoulder arthroplasty suffer from many disadvantages.

For example, since the glenoid component is subject to various types of loading by the head portion of the humeral component, the glenoid component must offer a stable and secure articulating surface. To achieve this, some glenoid components provide pegs that are inserted and cemented into holes bored into the glenoid cavity. However, such existing pegged glenoid components also exhibit several disadvantages. For example, some of the pegged glenoid components utilize up to five pegs to stabilize and secure the glenoid component to the scapula. Such glenoid components increase the amount of bone tissue removed, while also increasing the labor and complexity of the shoulder arthroplasty. Other pegged glenoid components may offer one or two larger diameter pegs that reduce the complexity of the shoulder arthroplasty. However, the larger diameter pegs also requires excess bone tissue to be removed that may not be practical in some patients. Furthermore, the use of one or two pegs may potentially reduce overall stability of the glenoid component, similar to a keeled glenoid.

Additionally, most prior art glenoid components only rely on the keel or pegs to secure the glenoid component to the scapula, via a cement mantle. These systems are typically rigid in fixation methods. In this regard, the prior art systems fail to provide a selection of coupling mechanisms which may best be used to address varying degenerative changes or specific muscular needs of a patient.

What is needed then is a glenoid component and associated surgical components for use in shoulder arthroplasty that does not suffer from the above-mentioned disadvantages. This in turn, will provide a glenoid component which is stable and secure, reduces the overall amount of bone tissue required to be removed, reduces inventory, reduces the overall surgical time and complexity, increases overall medial surface area, enhances and increases attachment strength and adaptivity without increasing overall peg diameter, provides a fully enhanced coupling mechanism and increased overall stability, and provides increased tensile and shear strength. It is, therefore, an object of the present invention to provide such a glenoid component and associated surgical components for use in shoulder arthroplasty.

SUMMARY

In accordance with the teachings of the present invention, an apparatus and method for shoulder arthroplasty is disclosed. The apparatus and method employs a glenoid component and other associated surgical components for use in the shoulder arthroplasty. In this regard, the glenoid component is adapted to be implanted into a scapula at the glenoid fossa or cavity and engaged by a head portion of a humeral component.

In one embodiment, a glenoid component is used for shoulder arthroplasty such that the glenoid component is adapted to be implanted into a scapula and engaged by a head of a humeral component. The glenoid component includes a body having a first articulating surface and a second medial surface opposite to the first articulating surface. The first articulating surface is adapted to be engaged by the head of the humeral component and the second medial surface is adapted to be secured to the scapula. A plurality of fixed pegs are provided, each having a first end adapted to engage a cavity formed in the scapula and a second end extending from the medial surface. A central peg fixation mechanism is provided that is configured to couple a central fixation peg to the medial surface.

In another embodiment, a system for use during shoulder arthroplasty is provided. The system has a glenoid component adapted to be implanted into a scapula and engaged by a head of a humeral component. The glenoid component includes, a body having a first spherical articulating surface and a second medial surface. The first spherical articulating surface is adapted to permit rotational movement of the head of the humeral component. A plurality of fixed coupling pegs are provided having a first end adapted to engage a cavity formed in the scapula. The medial portion has a central stem fixation mechanism, and a depending central stem.

In another embodiment, a method for implanting a medical device is disclosed. A glenoid prosthetic having a plurality of fixed pegs and a center fixation peg coupling mechanism is provided. The method includes machining a scapula to form a resected glenoid. A plurality of fixed peg accepting holes are machined in the resected glenoid. Further, the scapula is machined to form a center fixation peg coupling member accepting aperture. The physician will then determine if a center fixation peg is needed. If a center peg is required, a center peg is coupled to a glenoid prosthetic. A central peg accepting aperture is optionally machined into the resected glenoid. The prosthetic is then coupled to the resected glenoid either with or without the attached central stem.

Use of the present invention provides an apparatus and method for shoulder arthroplasty, and specifically, a glenoid component and associated surgical components for use in shoulder arthroplasty. As a result, the aforementioned disadvantages associated with the currently available glenoid components and associated surgical components for shoulder arthroplasty have been substantially reduced or eliminated. It should be understood that the detailed description and specific examples, while indicating the preferred embodiment of the invention, are intended for purposes of illustration only and are not intended to limit the scope of the invention.

DRAWINGS

The drawings described herein are for illustration purposes only and are not intended to limit the scope of the present disclosure in any way.

FIGS. 19A and 18B represent perspective and cross-sectional views of a glenoid prosthetic according to the present teachings;

DETAILED DESCRIPTION

The following description is merely exemplary in nature and is not intended to limit the present disclosure, application, or uses.

Figure 1:
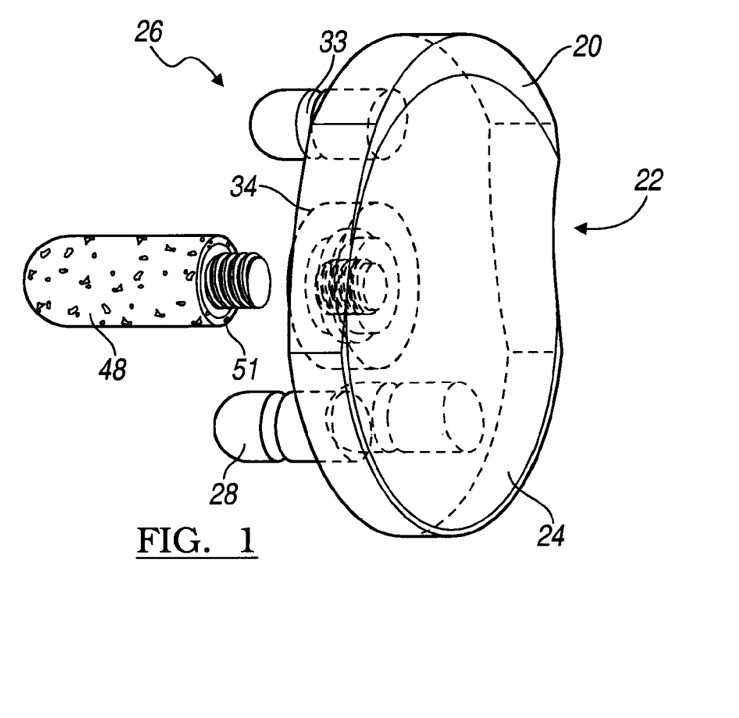
FIG. 1 represents an exploded view of a modular glenoid according to the present teachings of the present disclosure.
Figure 2:
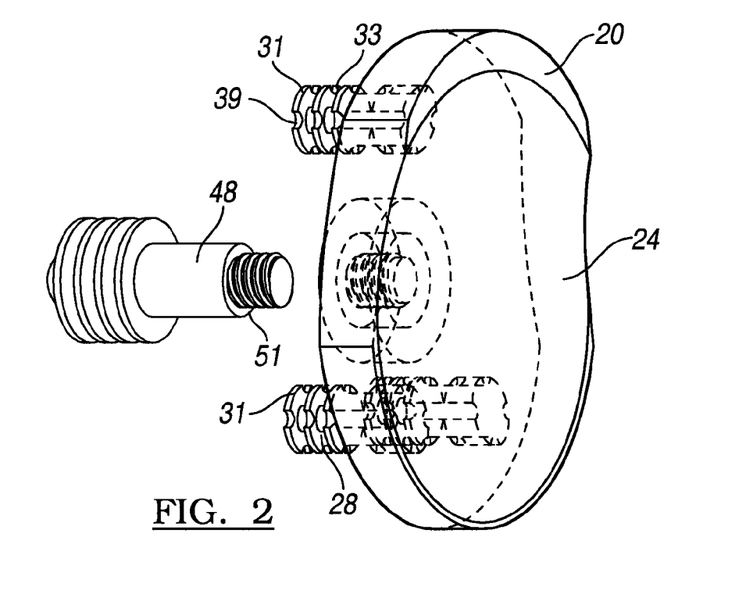
FIG. 2 represents a second glenoid according to the present teachings.

Referring generally to FIGS. 1 and 2 which represent perspective views of the modular glenoid component according to the teachings of the present application. Shown is a glenoid prosthetic 20. The glenoid prosthetic 20 has a first side 22 having a generally spherical articulating surface 24 and a second coupling side 26. The spherical articulating surface 24 is adapted to permit rotational and translational movement of the head of the humeral component (not shown) or natural humerus. The coupling side 26 can include one or more fixed coupling stems 28 that are configured to couple the glenoid to a plurality of apertures defined within a resected glenoid.

The coupling stems 28 can be configured to include a first superior fixed peg 28 and a pair of second inferior fixed pegs 28, each fixed peg 28 positioned on the coupling side 26 to form the corners of a triangle and, preferably, an isosceles triangle. The coupling stems 28 can take on various forms. In this regard, the fixed stems 28 can have a relatively smooth profile which define annular and/or longitudinal grooves 33. As described below, the grooves 33 can be configured to accept bone cement to fixably couple the peg to apertures 35 defined within a resected glenoid 37. As shown in FIG. 2, the fixed glenoid stems 28 can have a plurality of aperture engaging flanges 31. Defined on the flanges 31 can be a plurality of grooves 39. These grooves 39 can be co-axial with grooves 33 defined by the stem 28.

Figure 3A:
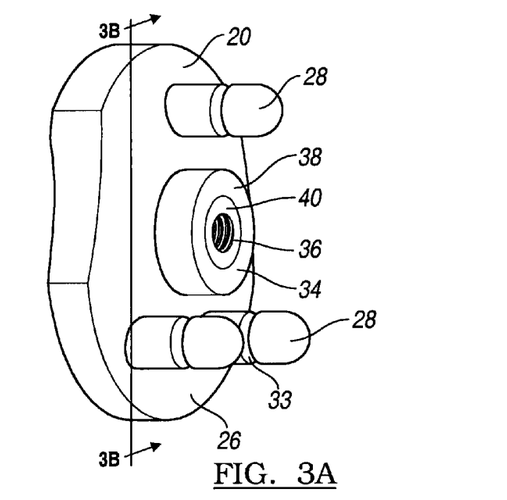
FIGS. 3A and 3B represent perspective and side views of the glenoid according to FIG. 1.
Figure 3B:
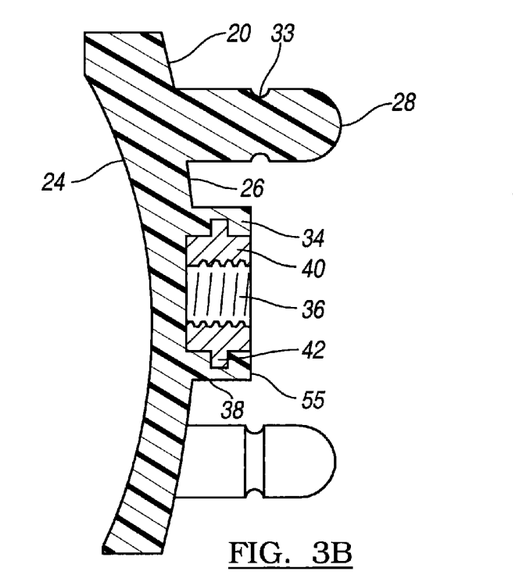
Figure 4A:
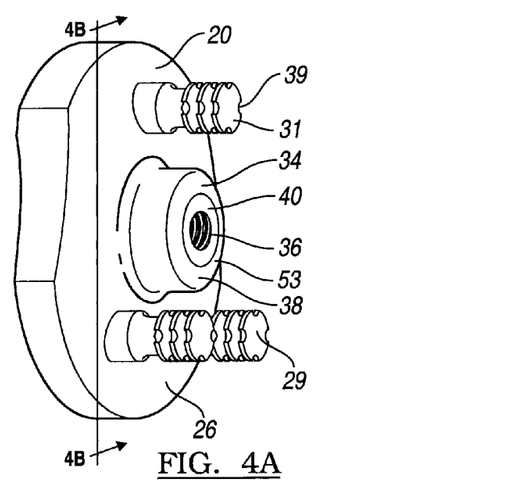
FIGS. 4A and 4B represent perspective and side views of the glenoid according to FIG. 2.
Figure 4B:
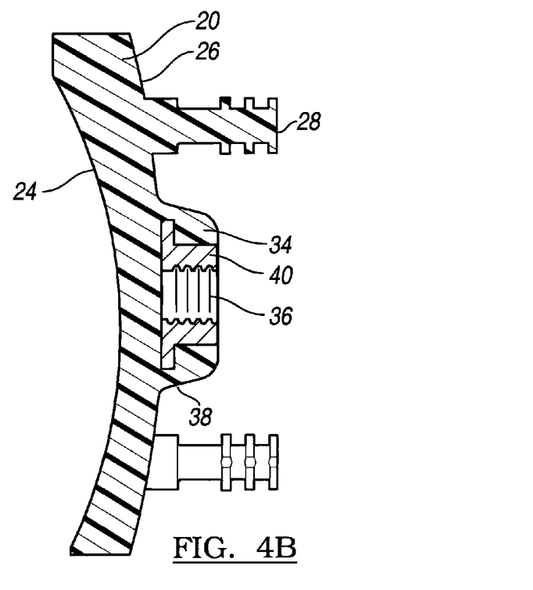
Figure 5A:
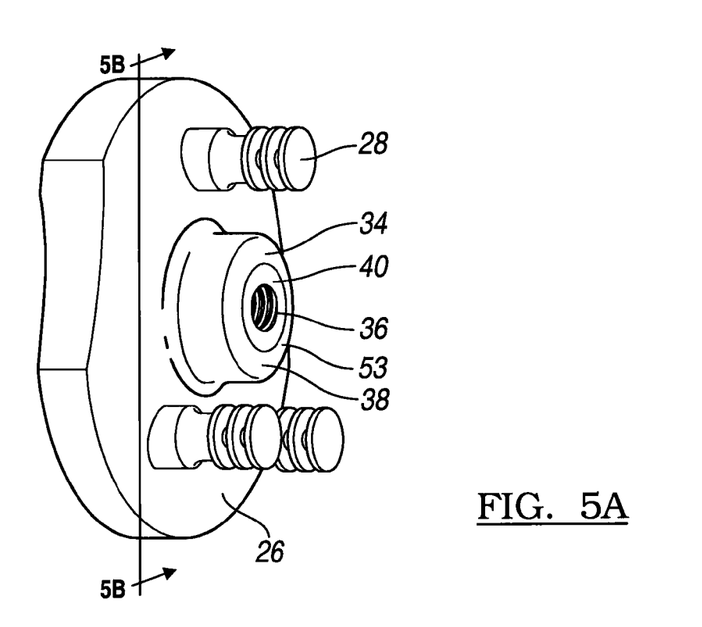
FIGS. 5A and 5B represent alternate perspective and cross-sectional views according to the present teachings.
Figure 5B:
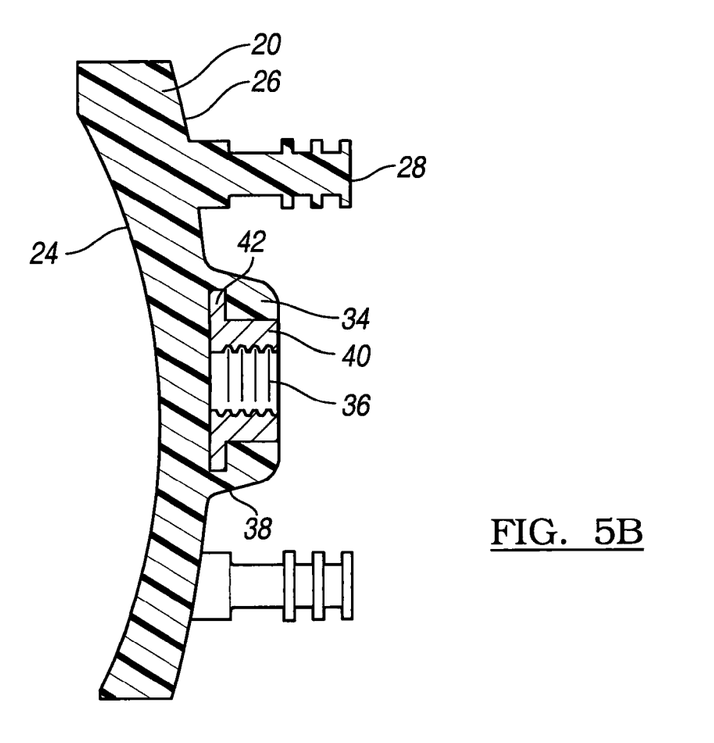

As best seen in FIGS. 3A-3B, the coupling side 26 of the glenoid 20 also defines a central stem coupling mechanism 34. The coupling mechanism 34 is configured to removably and selectively couple a central fixation peg 48 to the coupling side 26. This mechanism can define male or female threaded portions which interface with the central stem 48. As shown, the coupling mechanism 34 can define a threaded coupling aperture 36 within a generally cylindrical body 38. As shown in FIGS. 4A-5B, this cylinder can have a flat or curved exterior surface. In this regard, it is envisioned the exterior surface can be tapered to transition into the coupling side 26. Disposed within the body 38 can be an internally threaded bushing 40. Defined on an exterior surface of the bushing 40 are optional coupling flanges 42 that are configured to couple the bushing 40 to the cylindrical body 38. This bushing can be coupled to the glenoid during a molding process, or the bushing can be press-fit into the coupling side 26.

FIGS. 6A-6E represent perspective and side views of the optional central coupling stems 48. Each of the central coupling stems 48 can have a threaded coupling member 50 which is configured to fixably interface the stem 48 with the threaded aperture 36 of the central coupling mechanism 34. The stems 48 further have a bearing surface or shoulder 51 configured to interface with a bearing surface or base 53 on the central coupling mechanism 34. Optionally, the stems 48 can have a textured coupling surface.

Figure 6A:
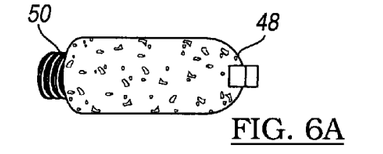
FIGS. 6A-6E represent perspective views of various stems usable in the glenoids shown in FIGS. 1-4B.
Figure 6B:
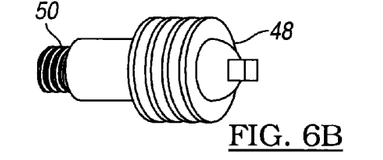
Figure 6C:
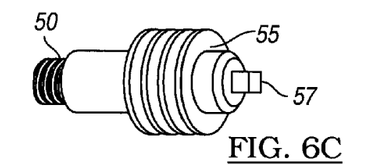
Figure 6D:
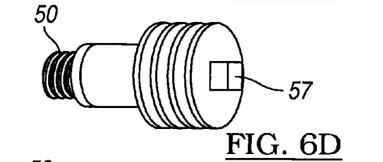
Figure 6E:
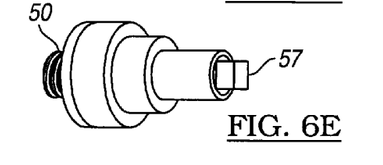

FIG. 6A represents a center peg 48 having a generally cylindrical fixation peg with an exterior powder metal coating. FIGS. 6B-6D represent central pegs having at least one aperture engaging flange. These flanges can either be used to interface with the interior of an aperture formed in the scapula or can be used to retain bone cement in the aperture. FIG. 6E represents a porous central peg having a stepped exterior surface. The stepped exterior surface has varying diameter portions.

Figures 7A, 7B, 7C:
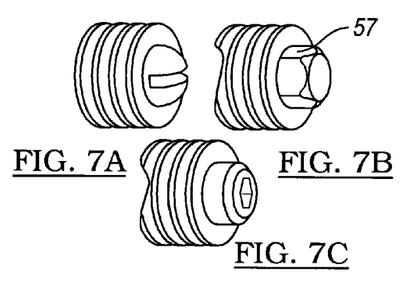
FIGS. 7A-7C represent various drive mechanisms.
Figure 8A:
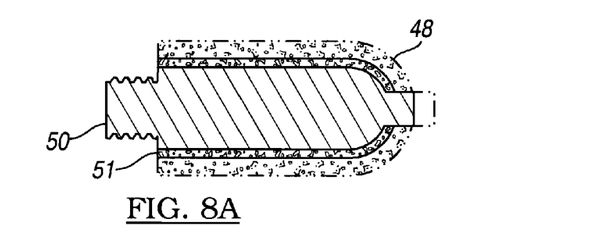
FIGS. 8A-8E represent cross-sectional views of the stems shown in FIGS. 6A-6E.
Figure 8B:
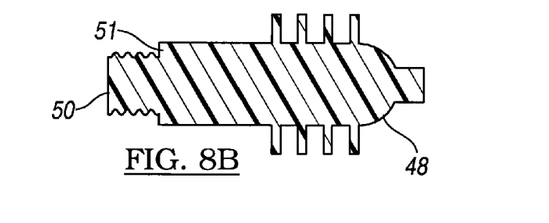
Figure 8C:
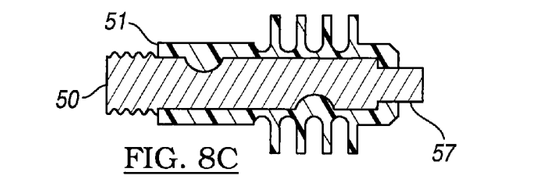
Figure 8D:
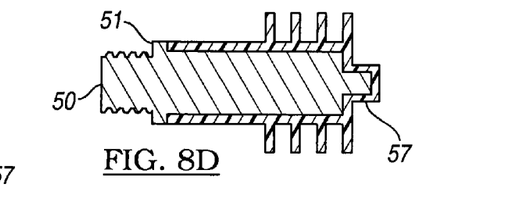
Figure 8E:
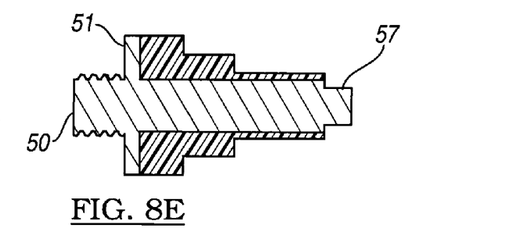

As shown, the central stem 48 can have various surface treatments. It is envisioned the stem can be formed of a biocompatible polymer, metallic or ceramic. Additionally, the central pegs can have surface treatment such as powder metal spray coating or other porous structures to facilitate the ingrowth of bone. As shown in FIGS. 7A-7C, optionally, the stems 48 can have drive surfaces 57 defined on a surface of the stem 48. These drive surfaces 57 can be a multi-faceted extension or a multi-faceted surface defined within a bore in the stem 48.

Shown in FIGS. 8A-8E, the stem can have various cross-sections. In this regard, the diameters of the stems can vary along the length of the stems 48. As shown in FIGS. 6B-6D, the stems 48 can have various coupling flanges 55 incorporated thereon. These coupling flanges 55 can be configured to have an exterior diameter which is less than, equal to, or greater than the corresponding diameter of a portion of an aperture disposed in the resected glenoid 37. Each of the stems 48 is configured to interface with a bearing surface on the central coupling mechanism 34.

Figure 9:
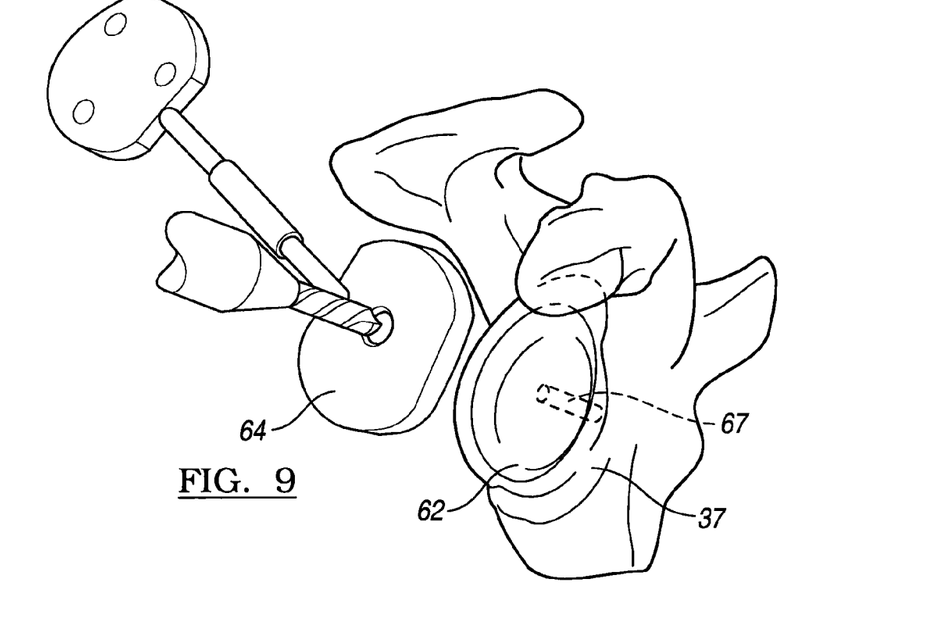
FIGS. 9-12 represent perspective views of the preparation of the glenoid to accept the prosthetic shown in FIGS. 1-8E.
Figure 10:
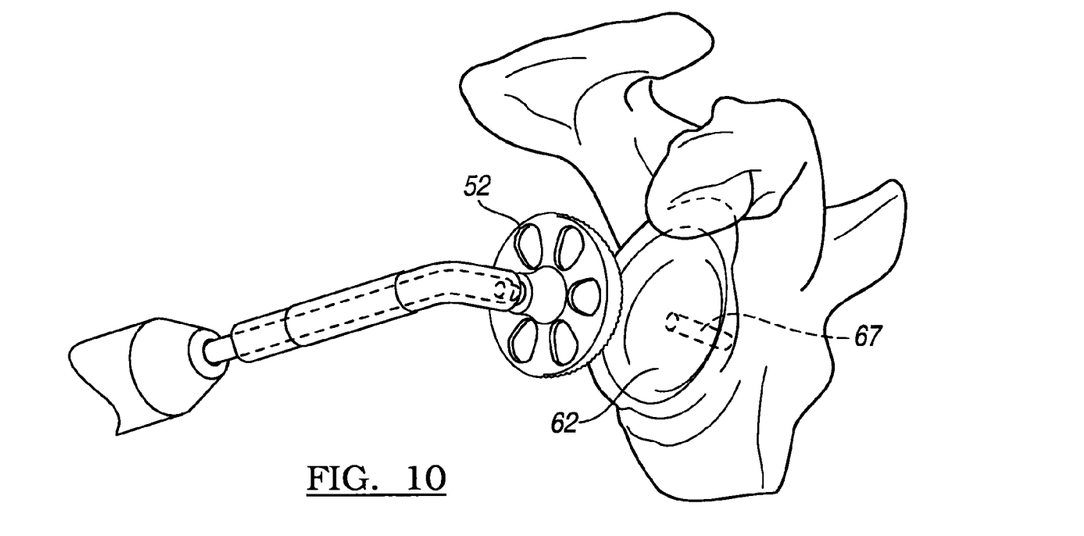

FIGS. 9-13 represent the preparation and insertion of the glenoid 20 according to the teachings herein. As shown in FIG. 9, a second drilling guide 64 can be used to position a central pilot hole 67 into the surface 62. After the preparation of a central guide hole 67, as shown in FIG. 10, the surface of the glenoid 62 is prepared using a rotating rasp or file 52. The scapula is then machined to form the resected glenoid 37. Shown is a rotating rasp 52 used to prepare a planar or curved glenoid surface to mate with the coupling side of the prosthetic 20.

Figure 11:
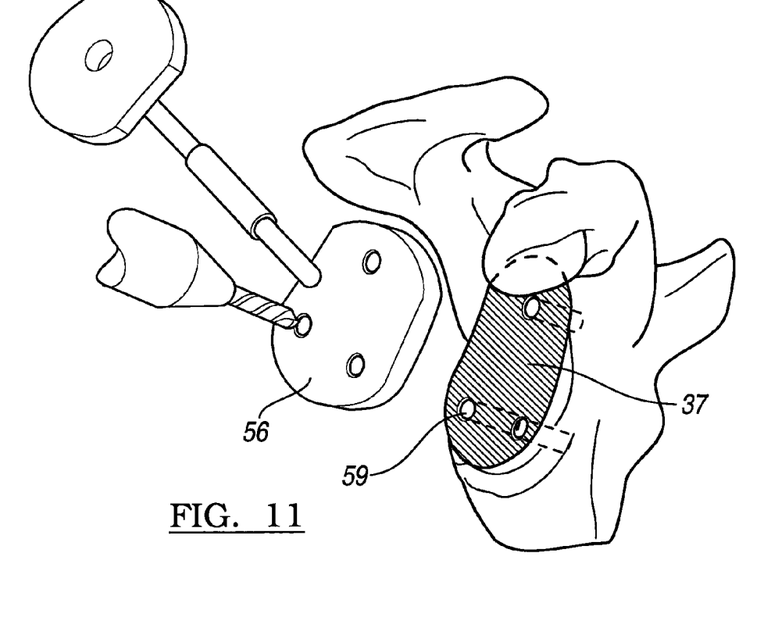
Figure 12:
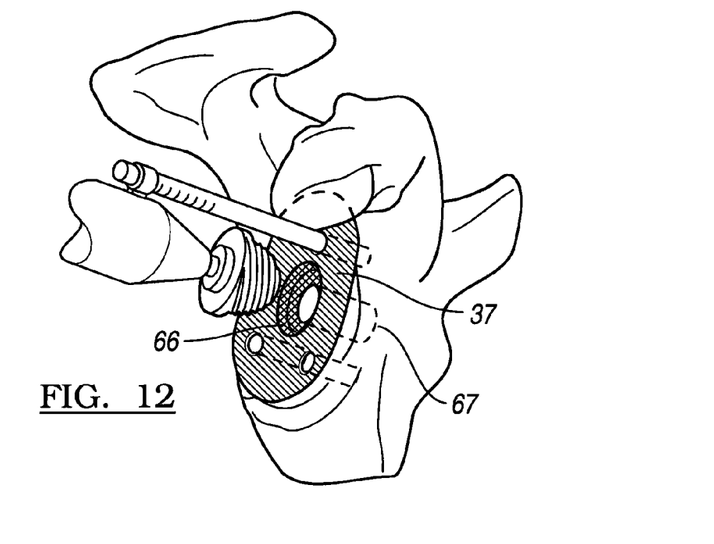

After the resection, a plurality of fixed peg accepting holes 59 are machined into the resected glenoid 37. FIG. 11 represents the use of a drilling guide 56 for the placement of holes within the resected glenoid 37. In this regard, it is envisioned that the drilling guide 56 be used to position the apertures for the acceptance of the fixed stems 28. As shown in FIG. 12, immediately about a central pilot hole, a surface 66 is prepared which is configured to accept the stem coupling mechanism 34. The center stem accepting aperture can be formed either prior to or after the preparation of the surface 66 to accept the stem coupling mechanism 34. At this point, the physician can determine if a central fixation peg 48 is needed. If the central peg 48 is needed, the physician will further determine a preferred central peg fixation surface and a preferred central peg fixation size. The appropriate peg 48 is then chosen and theadably coupled to the glenoid 20 so as to cause engagement of the stem bearing surface 51 with the bearing surface 53 on the central coupling mechanism 34.

Figure 13:
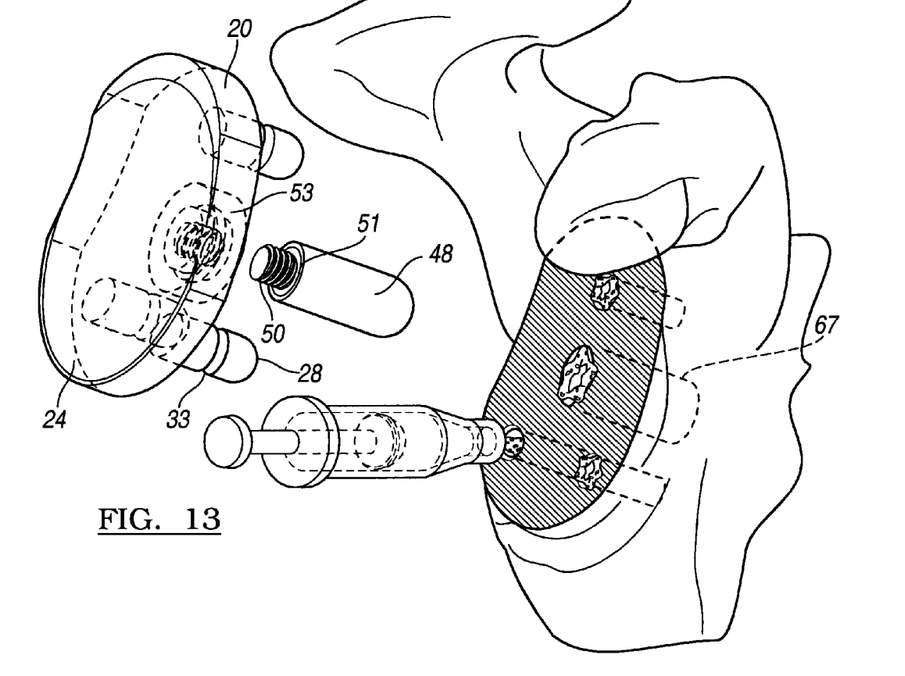
FIG. 13 represents the implantation of the glenoid shown in FIG. 1.

As shown in FIG. 13, it is envisioned that bone cement or biological materials can be injected into the apertures defined within the resected glenoid 37. These materials can be inserted into the holes configured to accept the fixed pegs or the central stem 48. It is equally envisioned that the central stem 48 can be inserted into the aperture so as to form an interference fit between the central stem 48 and the aperture. With the appropriate coupling stem 48 fixed to the bushing within the coupling mechanism 34, proper coupling of the glenoid 20 can occur. In this regard, the central stem 48 is threadably coupled to an aperture within the central stem coupling mechanism 34. The fixed and central stems are positioned within the apertures to couple the glenoid member 20 to the resected glenoid 37.

Figure 14:
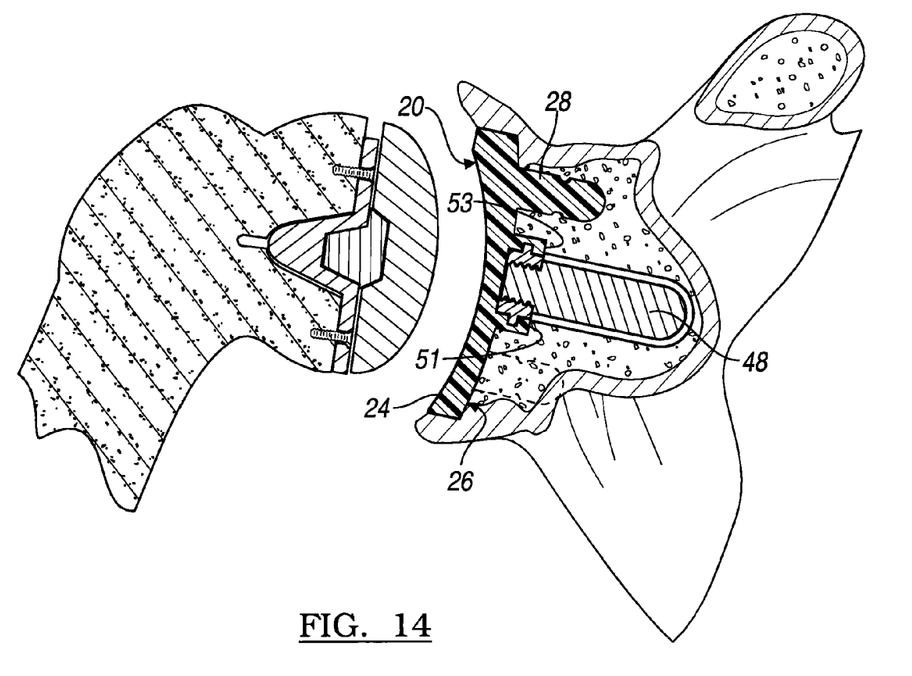
FIG. 14 represents a side cross-sectional view of a glenoid according to the present teachings implanted into a resected glenoid.

FIG. 14 represents a cross-sectional view of an implanted glenoid 20. Shown is the relationship between the articulating surface 24, fixed stems 28, and the central stem 48. Optionally, the coupling side 26 can be bonded to the resected glenoid using bone cement and further can have surface treatments to facilitate bonding. Further shown is the central stem 48 in relation to the threaded aperture 36 of the central stem coupling mechanism 34.

Figure 15:
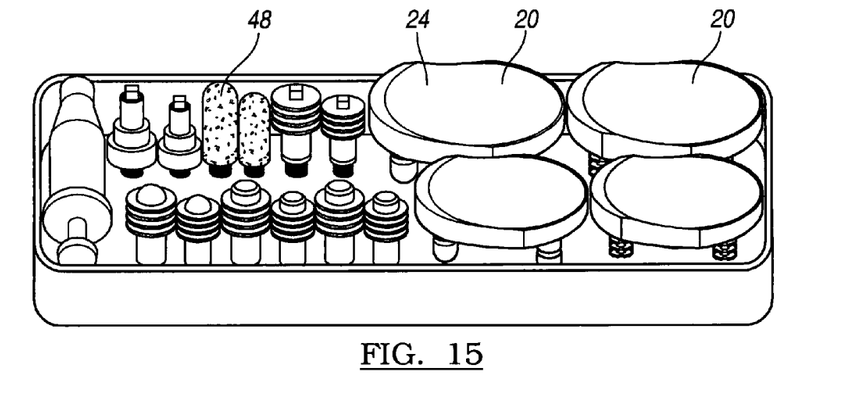
FIG. 15 represents a system of modular glenoid components according to the present teachings.

FIG. 15 represents a system of prosthetic components as described above. Shown are various glenoid prosthetics 20 as well as various size and shaped central stem portions 48. These stems 48 have various exterior surface treatments and configurations as well as varying lengths and diameters. It is envisioned that the system also includes the appropriate types of bone fixation cement, cutting members, cutting pattern guides, as well as humeral head and fixation stem prosthetics.

Figure 16:
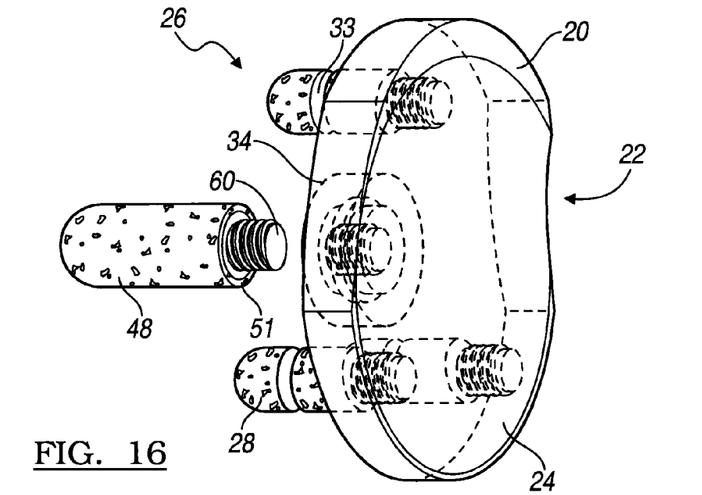
FIGS. 16 and 17 represent perspective and cross-sectional views of an alternate glenoid component according to the present teachings.
Figure 17:
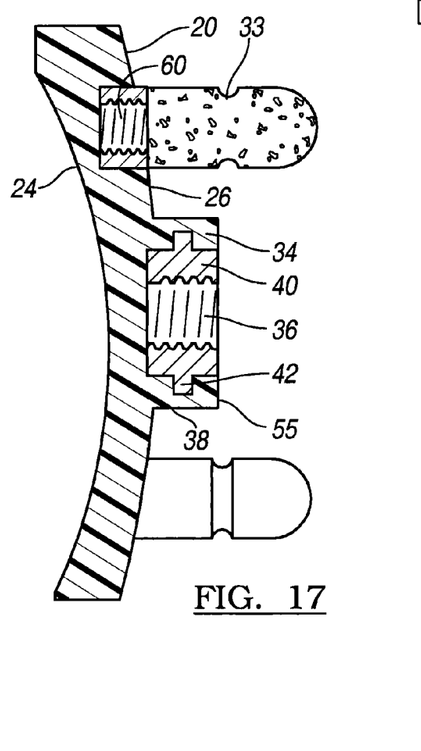

Referring generally to FIGS. 16 and 17 which represent perspective and cross sectional views of the modular glenoid component according to an alternate teaching. Shown is a glenoid prosthetic 20. The glenoid prosthetic 20 has a first side 22 having a generally spherical articulating surface 24 and a second coupling side 26. The spherical articulating surface 24 is adapted to permit rotational and translational movement of the head of the humeral component (not shown) or natural humerus. The coupling side 26 can include one or more removable peripheral coupling stems 28 that are configured to couple the glenoid to a plurality of apertures defined within a resected glenoid.

The coupling stems 28 can be configured to include a first superior removable peg 28 and a pair of second inferior removable pegs 28. Each removable peg 28 is positioned on the coupling side 26 to form the corners of a triangle and, optionally, an isosceles triangle. The coupling pegs 28 can take on various forms. In this regard, the pegs 28 can have a relatively smooth profile which define annular and/or longitudinal grooves 33. As described above, the grooves 33 can be configured to accept bone cement to fixably couple the peg to apertures 35 defined within a resected glenoid 37. As shown in FIG. 17, the fixed glenoid stems 28 can have a porous outer coating such as Regenerex (see also FIG. 8A).

It is envisioned that the pegs 28 can be coupled to the coupling side via a threaded member or a locking taper. The threaded member 60 can have a self tapping thread configured to engage a threaded hole formed in the coupling side 26. Additionally, the threaded member 60 can be coupled to a bushing integrally molded into the glenoid prosthetic 20. Optionally, the threaded bushing can have a textured exterior surface or retaining flange to facilitate the integration thereof. Each peg has a flat bearing surface configured to bear against a flat bearing surface on the medial side or the bushing.

Figure 18A:
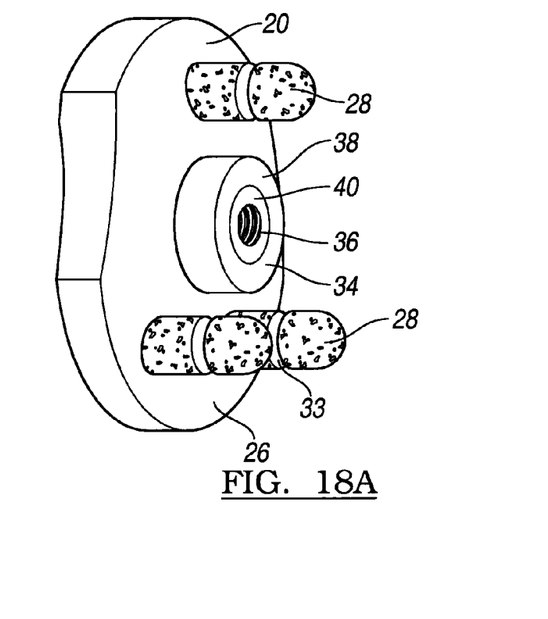
FIGS. 18A and 18B represent an integrally molded stem and glenoid component according to the present teachings.
Figure 18B:
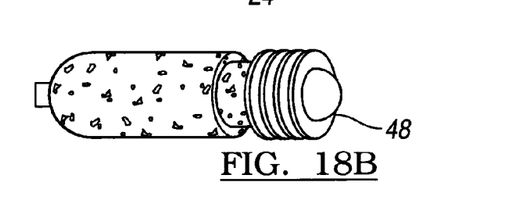

As shown in FIGS. 18A and 18B, the coupling stem 48 can be integrally molded into the glenoid prosthetic 20. In this regard, the premachined stem 48 can have a porous coating integrally formed thereon. Additionally formed on the stem 28 can be a plurality of flanges used to fix the coupling stem into the glenoid prosthetic and protruding from the coupling surface 26. As described above, the central fixation stem can be coupled to the threaded central bore 36 formed in the plastic or an inserted bushing.

As shown in FIG. 18B, the stem 28 can be formed of a titanium substrate 70 with an applied Regenerex layer. The Regenerex layer can be machined prior to being placed within a mold. A blank which is used to form the glenoid body 20 can then be formed by molding an e-poly block over the titanium stem substrates. The polymer can be formed of sintered UHMWPE 1050 powder. This polymer can be doped with vitamin E for six hours and then homogenized for 400 hours. The polymer can then be machined into final form after molding. In this regard, the bearing and interface surfaces 24, 20 can be machined into the glenoid prosthetic 20.

Figure 19A:
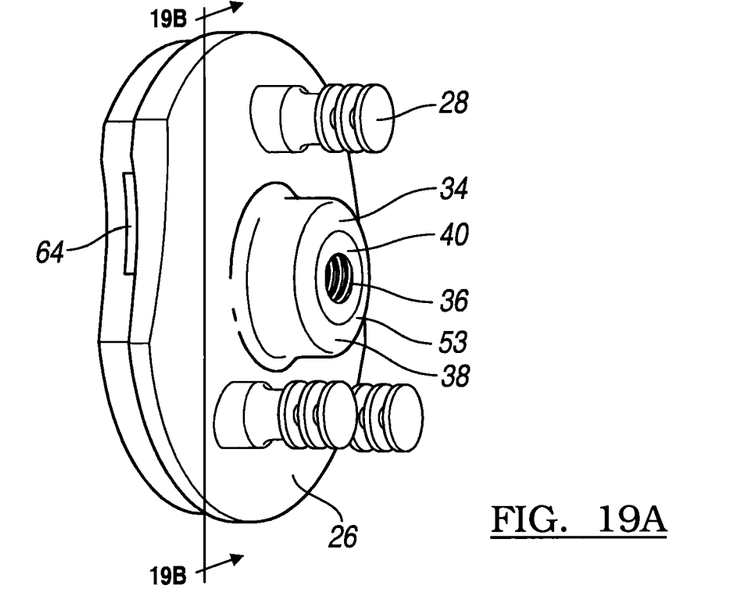
Figure 19B:
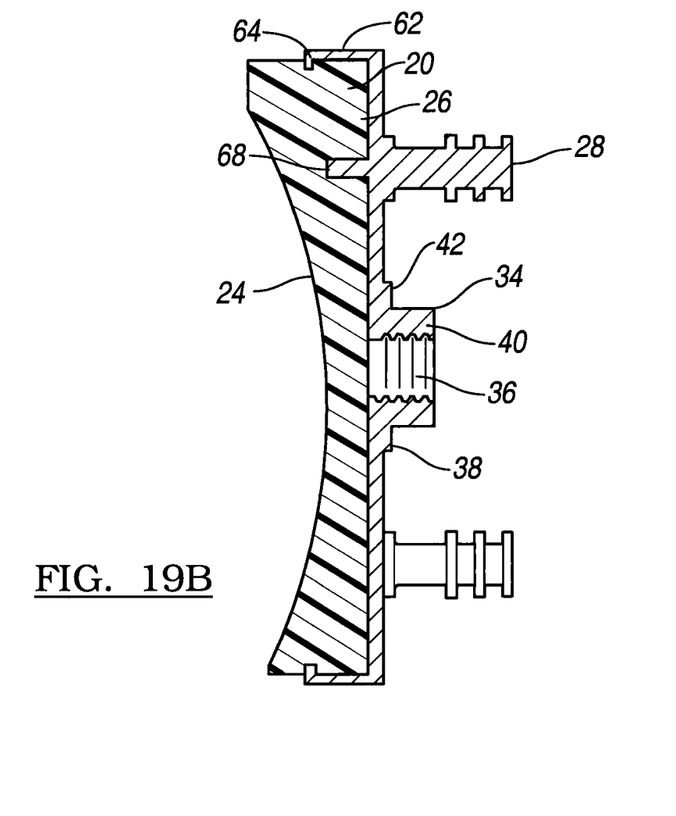

FIGS. 19A and 19B represent perspective and cross sectional views of the modular glenoid component according to an alternate teaching. The glenoid prosthetic 20 has a first side 22 having a generally spherical articulating surface 24 and a second coupling side 26. The spherical articulating surface 24 is adapted to permit rotational and translational movement of the head of the humeral component (not shown) or natural humerus. The coupling side 26 can be formed of a tray 62 which includes one or more fixed peripheral coupling stems 28 that are configured to couple the glenoid to a plurality of apertures defined within a prepared glenoid. The polymer bearing can be integrally molded onto the tray 62, or can be snapped onto the tray 62 using a snap feature 64. Alternatively, the bearing can be coupled to the tray 62 using integral coupling pegs 68. The tray incorporated pegs 68 can have surface treatments or flanges to facilitate fixation.

Figure 20:
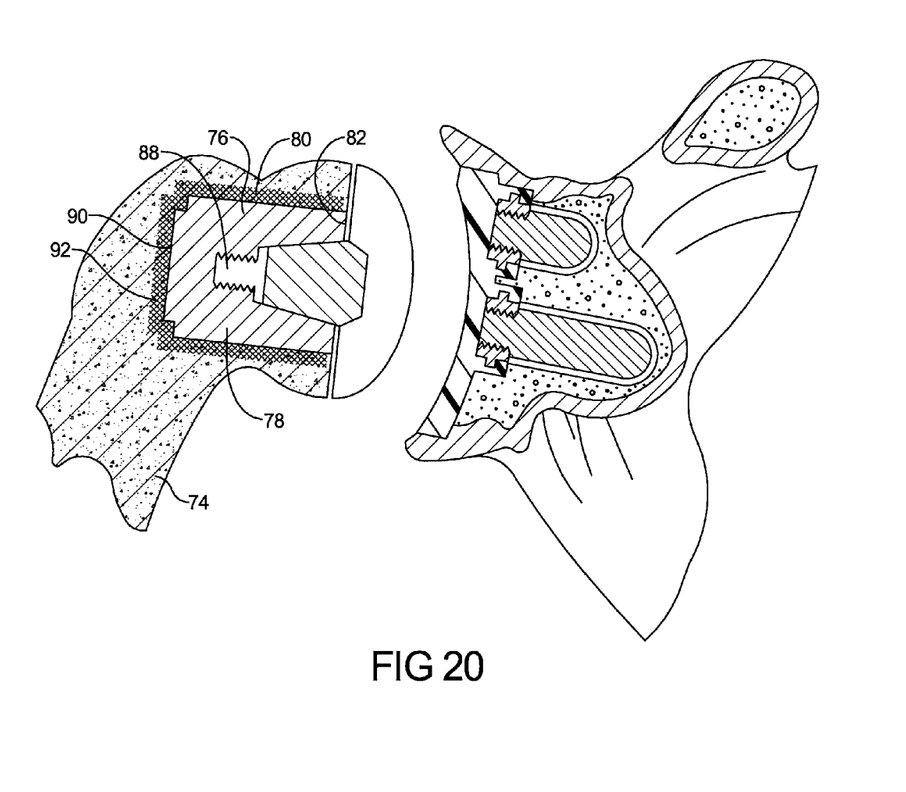
FIG. 20 represents a cross-sectional view of an alternate humeral head prosthetic according to the present teachings.

FIG. 20 represents a cross-sectional view of an alternate humeral component according to the present teachings. Shown is a resected humerus 74 having a coupling member 76 disposed therein. The coupling member 76 has a generally cylindrical body 78 having a plurality of bone engaging flanges 80 disposed thereon. The generally cylindrical body 78 has an outer surface having a generally constant exterior diameter. Disposed at a proximal end 82 of the body is a generally planar and circular head coupling surface 86. The head coupling surface 86 has an associated coupling taper 88 configured to couple a humeral head 92 to the coupling member 76.

Figure 21:
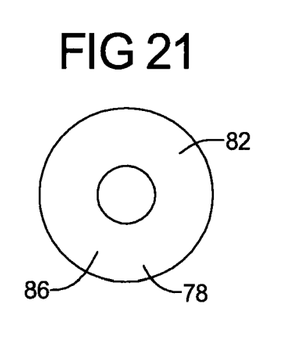
FIGS. 21-24 represent top and side views of various coupling members according to the present teachings.
Figure 22:
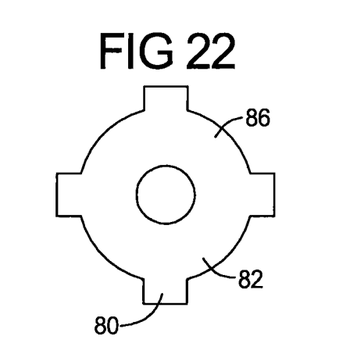
Figure 23:
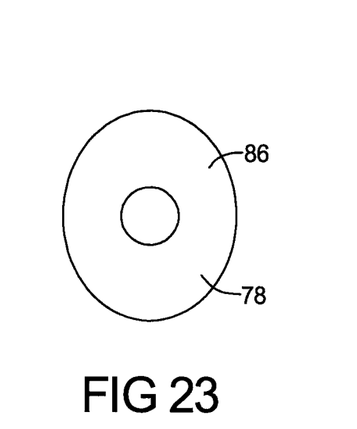

As shown in FIGS. 21 and 23, the body can have a circular or an oblong circular cross-sectional shape. It is envisioned the shape can be formed into the resected humerus 74 using a rotating cutting member and a cutting measurement guide. The coupling member 76 can be impacted into an aperture formed into the resected head or head and neck of the humerus 74. In this regard, an impaction tool (not shown) can be coupled to a threaded hole 88 defined within the body. Slots can be formed into the humerus 74 to accept the retaining flanges therein. Optionally, the entire prosthetic can be placed within only the head or head and neck, and not into the medullary canal.

Figure 24:
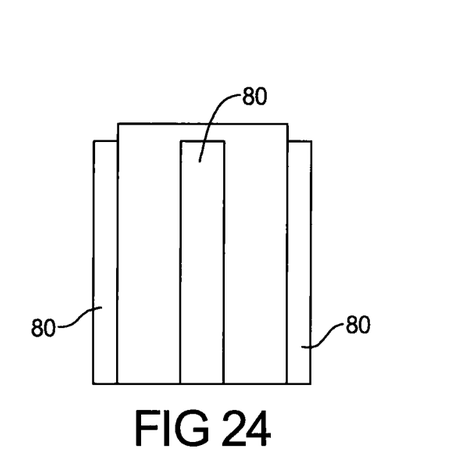
Figure 25:
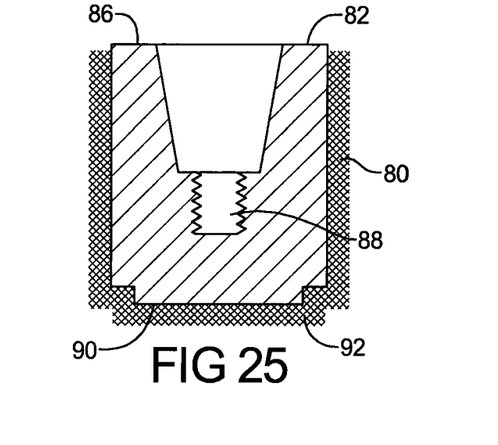
FIG. 25 represents a cross-sectional view of the coupling member shown in FIG. 22.

As shown in FIGS. 24 and 25, the exterior surface of the body can be uncoated or at least be partially coated with metallic powder coating, or coatings such as Regenerex, configured to promote boney in-growth. This powder metal or bone growth promoter can also cover the generally planar interface surface 90 at the distal end 92 of the coupling member.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations)

What is claimed is:

1. A glenoid prosthetic comprising:
   a glenoid body having an articulating surface operable to be engaged by the head of a humeral component or a natural humerus, a medial surface operable to be attached to a resected glenoid of a scapula, and a plurality of threaded bores formed by bushings molded into said glenoid body; and
   a plurality of coupling stems threadably attached to said glenoid body at said medial surface via said plurality of threaded bores and operable to be individually received within apertures formed in said resected glenoid, said plurality of coupling stems each including a porous outer coating and a flat bearing surface operable to engage a flat bearing surface of a respective one of said bushings when said plurality of coupling stems are attached to said bushings.

2. The glenoid prosthetic of claim 1, wherein said plurality of coupling stems are removably attached to said glenoid body.

3. The glenoid prosthetic of claim 1, wherein said plurality of coupling stems each include a metal substrate, said porous outer coating applied to said metal substrate.

4. The glenoid prosthetic of claim 1, further comprising an annular groove circumferentially surrounding each one of said plurality of coupling stems.

5. The glenoid prosthetic of claim 4, wherein said annular groove is formed in said porous outer coating.

6. A glenoid prosthetic comprising:
   a glenoid body having an articulating surface operable to be engaged by the head of a humeral component or a natural humerus, a medial surface operable to be attached to a resected glenoid of a scapula, and a plurality of threaded bores formed by bushings molded into said glenoid body; and a plurality of coupling stems threadably attached to said glenoid body at said medial surface via said plurality of threaded bores and operable to be individually received within apertures formed in said resected glenoid, said plurality of coupling stems cooperating to form the corners of a triangle and each including a flat bearing surface operable to engage a flat bearing surface of a respective one of said bushings when said plurality of coupling stems are attached to said bushings.

7. The glenoid prosthetic of claim 6, wherein said plurality of coupling stems each include a porous outer coating.

8. The glenoid prosthetic of claim 7, wherein said plurality of coupling stems each include a metal substrate, said porous outer coating applied to said metal substrate.

9. The glenoid prosthetic of claim 7, further comprising an annular groove circumferentially surrounding each one of said plurality of coupling stems.

10. The glenoid prosthetic of claim 9, wherein said annular groove is formed in said porous outer coating.

* * * * *